US012336922B2

(12) United States Patent
Garcia

(10) Patent No.: US 12,336,922 B2
(45) Date of Patent: Jun. 24, 2025

(54) METHOD OF USE FOR DELIVERY SYSTEM FOR RADIALLY CONSTRICTING A STENT GRAFT

(71) Applicant: Bolton Medical, Inc., Sunrise, FL (US)

(72) Inventor: Eduardo Alejandro Garcia, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 0 days.

(21) Appl. No.: 18/226,477

(22) Filed: Jul. 26, 2023

(65) Prior Publication Data

US 2024/0197503 A1 Jun. 20, 2024

Related U.S. Application Data

(63) Continuation of application No. 17/690,775, filed on Mar. 9, 2022, now Pat. No. 11,744,722, which is a
(Continued)

(51) Int. Cl.
*A61F 2/95* (2013.01)
*A61F 2/07* (2013.01)
(Continued)

(52) U.S. Cl.
CPC ............ *A61F 2/95* (2013.01); *A61F 2/07* (2013.01); *A61F 2/954* (2013.01); *A61F 2/9662* (2020.05);
(Continued)

(58) Field of Classification Search
CPC ...... A61F 2220/0075; A61F 2/07; A61F 2/95; A61F 2/9517; A61F 2/954; A61F 2/9522;
(Continued)

(56) References Cited

U.S. PATENT DOCUMENTS 5,242,452 A 9/1993 Inoue
5,507,769 A 4/1996 Marin et al.
(Continued)

FOREIGN PATENT DOCUMENTS

AU 2016256777 B1 4/2017
CN 102413794 A 4/2012
(Continued)

OTHER PUBLICATIONS

Extended European Search Report for EP Application No. 21153107.4 dated May 18, 2021.
(Continued)

*Primary Examiner* — Majid Jamialahmadi
(74) *Attorney, Agent, or Firm* — Stephen J. Kenny; Emily H. Yasharpour; Foley Hoag LLP

(57) ABSTRACT

A stent graft delivery system includes a handle, a guidewire catheter extending distally from the handle, at least one tube, and at least one wire extending through the at least one tube, wherein each wire of the stent graft delivery system is configured as a loop at the distal end of the tube. The stent graft delivery system can be employed to implant stent grafts in a patient to thereby treat, for example, an aortic aneurysm spanning a region of an aorta that includes at least one arterial branch.

20 Claims, 13 Drawing Sheets

Related U.S. Application Data continuation of application No. 16/379,423, filed on Apr. 9, 2019, now Pat. No. 11,291,572, which is a continuation of application No. PCT/US2018/019355, filed on Feb. 23, 2018.

(60) Provisional application No. 62/463,018, filed on Feb. 24, 2017.

(51) Int. Cl.
*A61F 2/954* (2013.01)
*A61F 2/966* (2013.01)

(52) U.S. Cl.
CPC ..... *A61F 2002/9511* (2013.01); *A61F 2/9517* (2020.05); *A61F 2002/9665* (2013.01); *A61F 2220/0075* (2013.01)

(58) Field of Classification Search
CPC ...... A61F 2002/9511; A61F 2002/9665; A61F 2002/9528
See application file for complete search history.

(56) References Cited

U.S. PATENT DOCUMENTS

| | | | |
|---|---|---|---|
| 5,713,948 A * | 2/1998 | Uflacker | A61F 2/966 623/1.23 |
| 5,873,906 A | 2/1999 | Lau et al. | |
| 6,280,464 B1 | 8/2001 | Hayashi | |
| 6,776,791 B1 | 8/2004 | Stallings et al. | |
| 7,435,253 B1 | 10/2008 | Hartley et al. | |
| 7,763,063 B2 | 7/2010 | Arbefeuille et al. | |
| 8,007,605 B2 | 8/2011 | Arbefeuille et al. | |
| 8,137,393 B2 | 3/2012 | Ishimaru et al. | |
| 8,172,895 B2 | 5/2012 | Anderson et al. | |
| 8,236,040 B2 | 8/2012 | Mayberry et al. | |
| 8,486,129 B2 | 7/2013 | Lautherjung | |
| 8,500,792 B2 | 8/2013 | Berra | |
| 8,926,693 B2 | 1/2015 | Duffy et al. | |
| 9,101,455 B2 | 8/2015 | Roeder et al. | |
| 9,101,506 B2 | 8/2015 | Arbefeuille et al. | |
| 9,226,814 B2 | 1/2016 | Jensen et al. | |
| 9,278,018 B2 | 3/2016 | Roeder | |
| 9,364,314 B2 | 6/2016 | Berra et al. | |
| 9,375,308 B2 | 6/2016 | Norris | |
| 9,439,751 B2 | 9/2016 | White et al. | |
| 9,592,112 B2 | 3/2017 | Arbefeuille et al. | |
| 9,827,123 B2 | 11/2017 | Arbefeuille et al. | |
| 9,861,503 B2 | 1/2018 | Barthold et al. | |
| 9,877,857 B2 | 1/2018 | Arbefeuille et al. | |
| 9,913,743 B2 | 3/2018 | Arbefeuille et al. | |
| 10,005,269 B2 | 6/2018 | Hall et al. | |
| 10,080,674 B2 | 9/2018 | Yuan et al. | |
| 10,292,850 B2 | 5/2019 | Vad et al. | |
| 10,299,951 B2 | 5/2019 | Arbefeuille et al. | |
| 10,390,930 B2 | 8/2019 | Arbefeuille et al. | |
| 10,478,320 B2 | 11/2019 | Shahriari | |
| 10,617,542 B2 | 4/2020 | Chakfe et al. | |
| 10,898,357 B2 | 1/2021 | Arbefeuille et al. | |
| 11,219,540 B2 | 1/2022 | Arbefeuille | |
| 11,291,572 B2 | 4/2022 | Garcia | |
| 11,376,145 B2 | 7/2022 | Arbefeuille et al. | |
| 11,491,003 B2 | 11/2022 | Arbefeuille et al. | |
| 11,730,584 B2 | 8/2023 | Arbefeuille | |
| 11,744,722 B2 | 9/2023 | Garcia | |
| 2002/0038144 A1* | 3/2002 | Trout, III | A61F 2/07 623/1.15 |
| 2002/0062133 A1 | 5/2002 | Gilson et al. | |
| 2002/0151956 A1 | 10/2002 | Chobotov et al. | |
| 2003/0233140 A1 | 12/2003 | Hartley et al. | |
| 2004/0073289 A1 | 4/2004 | Hartley | |
| 2005/0049674 A1 | 3/2005 | Berra et al. | |
| 2005/0119722 A1 | 6/2005 | Styrc et al. | |
| 2005/0154444 A1 | 7/2005 | Quadri | |
| 2006/0004433 A1 | 1/2006 | Greenberg et al. |
| 2006/0015171 A1 | 1/2006 | Armstrong |
| 2006/0020319 A1 | 1/2006 | Kim et al. |
| 2006/0184226 A1 | 8/2006 | Austin |
| 2007/0043425 A1 | 2/2007 | Hartley et al. |
| 2007/0213805 A1 | 9/2007 | Schaeffer et al. |
| 2007/0233223 A1 | 10/2007 | Styrc |
| 2008/0082154 A1 | 4/2008 | Tseng et al. |
| 2008/0132988 A1 | 6/2008 | Jordan |
| 2008/0294234 A1 | 11/2008 | Hartley et al. |
| 2009/0248135 A1 | 10/2009 | Bruszewski et al. |
| 2010/0114290 A1 | 5/2010 | Rasmussen et al. |
| 2010/0234932 A1 | 9/2010 | Arbefeuille et al. |
| 2010/0268319 A1 | 10/2010 | Bruszewski et al. |
| 2011/0190862 A1 | 8/2011 | Bashiri et al. |
| 2012/0172965 A1 | 7/2012 | Kratzberg et al. |
| 2012/0323302 A1 | 12/2012 | Brinser |
| 2013/0116773 A1 | 5/2013 | Roeder et al. |
| 2013/0158648 A1 | 6/2013 | Hartley et al. |
| 2013/0289713 A1 | 10/2013 | Pearson et al. |
| 2014/0046429 A1 | 2/2014 | Cragg et al. |
| 2014/0180378 A1 | 6/2014 | Roeder |
| 2014/0336745 A1 | 11/2014 | Barthold et al. |
| 2015/0051691 A1 | 2/2015 | Zukowski et al. |
| 2015/0105819 A1 | 4/2015 | Becking et al. |
| 2015/0105849 A1 | 4/2015 | Cohen et al. |
| 2015/0202065 A1 | 7/2015 | Shalev et al. |
| 2015/0265444 A1 | 9/2015 | Kitaoka |
| 2016/0120667 A1 | 5/2016 | Bolduc et al. |
| 2016/0250050 A1 | 9/2016 | Lim et al. |
| 2016/0278910 A1 | 9/2016 | Kelly |
| 2016/0302950 A1 | 10/2016 | Marmur et al. |
| 2017/0281382 A1 | 10/2017 | Lostetter et al. |
| 2019/0231514 A1 | 8/2019 | Arbefeuille |
| 2019/0231568 A1 | 8/2019 | Garcia |
| 2019/0269498 A1 | 9/2019 | Arbefeuille et al. |
| 2019/0269537 A1 | 9/2019 | Arbefeuille |
| 2019/0321207 A1 | 10/2019 | Arbefeuille et al. |
| 2019/0350694 A1 | 11/2019 | Arbefeuille et al. |
| 2021/0100669 A1 | 4/2021 | Arbefeuille et al. |
| 2022/0160529 A1 | 5/2022 | Arbefeuille et al. |
| 2022/0192851 A1 | 6/2022 | Garcia |
| 2022/0313464 A1 | 10/2022 | Arbefeuille et al. |
| 2023/0048537 A1 | 2/2023 | Arbefeuille et al. |
| 2023/0338133 A1 | 10/2023 | Arbefeuille |

FOREIGN PATENT DOCUMENTS

| | | |
|---|---|---|
| CN | 102711664 A | 10/2012 |
| CN | 104027187 A | 9/2014 |
| CN | 104114201 A | 10/2014 |
| CN | 105832447 A | 8/2016 |
| CN | 105943213 A | 9/2016 |
| CN | 106344208 A | 1/2017 |
| DE | 102012101103 B3 | 7/2013 |
| EP | 2471498 A1 | 7/2012 |
| EP | 2501334 A1 | 9/2012 |
| EP | 2735283 A1 | 5/2014 |
| EP | 2740440 A2 | 6/2014 |
| EP | 2745812 A1 | 6/2014 |
| EP | 3040054 A1 | 7/2016 |
| EP | 3146993 A1 | 3/2017 |
| EP | 3187155 A1 | 7/2017 |
| EP | 3272319 A1 | 1/2018 |
| EP | 3320881 A1 | 5/2018 |
| EP | 3395302 A1 | 10/2018 |
| EP | 3733124 A1 | 11/2020 |
| GB | 2464978 A | 5/2010 |
| WO | WO-96/36297 A1 | 11/1996 |
| WO | WO-1997/03624 A1 | 2/1997 |
| WO | WO-1997/25002 A1 | 7/1997 |
| WO | WO-1997/48350 A1 | 12/1997 |
| WO | WO-2001/60285 A1 | 8/2001 |
| WO | WO-2002/083038 A2 | 10/2002 |
| WO | WO-2006/037086 A1 | 4/2006 |
| WO | WO-2007/115017 A1 | 10/2007 |
| WO | WO-2009/148594 A1 | 12/2009 |
| WO | WO-2010/105195 A2 | 9/2010 |
| WO | WO-2012/116368 A2 | 8/2012 |

(56) References Cited

FOREIGN PATENT DOCUMENTS

| WO | WO-2012/145823 A1 | 11/2012 |
| WO | WO-2014/162306 A2 | 10/2014 |
| WO | WO-2015/070792 A1 | 5/2015 |
| WO | WO-2016/122862 A1 | 8/2016 |
| WO | WO-2017/106156 A1 | 6/2017 |
| WO | WO-2018/183563 A1 | 10/2018 |
| WO | WO-2019/040326 A1 | 2/2019 |

OTHER PUBLICATIONS

Extended European Search Report for EP Application No. 22150465.7 dated Jun. 30, 2022.
International Preliminary Report on Patentability for International Application No. PCT/US2018/019342 dated Aug. 27, 2019.
International Preliminary Report on Patentability for International Application No. PCT/US2018/019344 dated Aug. 27, 2019.
International Preliminary Report on Patentability for International Application No. PCT/US2018/019355 dated Aug. 27, 2019.
International Preliminary Report on Patentability for International Application No. PCT/US2018/019356 dated Aug. 27, 2019.
International Search Report and Written Opinion for International Application No. PCT/US/2018/019355 dated May 22, 2018.
International Search Report and Written Opinion for International Application No. PCT/US2018/019342 dated May 22, 2018.
International Search Report and Written Opinion for International Application No. PCT/US2018/019344 dated May 16, 2018.
International Search Report and Written Opinion for International Application No. PCT/US2018/019356 dated May 16, 2018.
International Search Report and Written Opinion for International Application No. PCT/US2018/019510 dated Jul. 11, 2018.
International Search Report and Written Opinion for International Application No. PCT/US2021/058526 dated Mar. 18, 2022.
Supplementary European Search Report for EP Application No. 21187803 dated Nov. 23, 2021.

\* cited by examiner

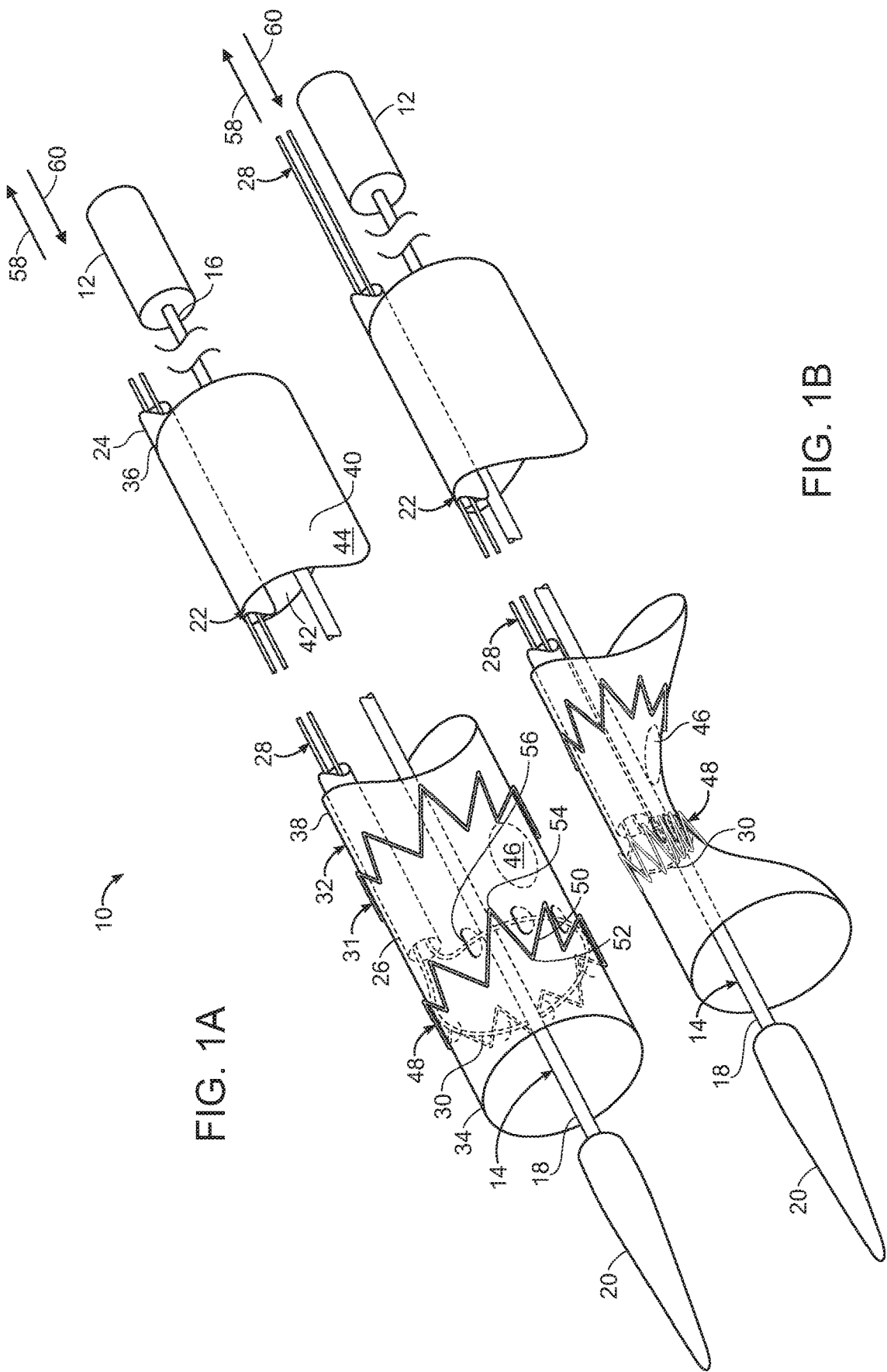

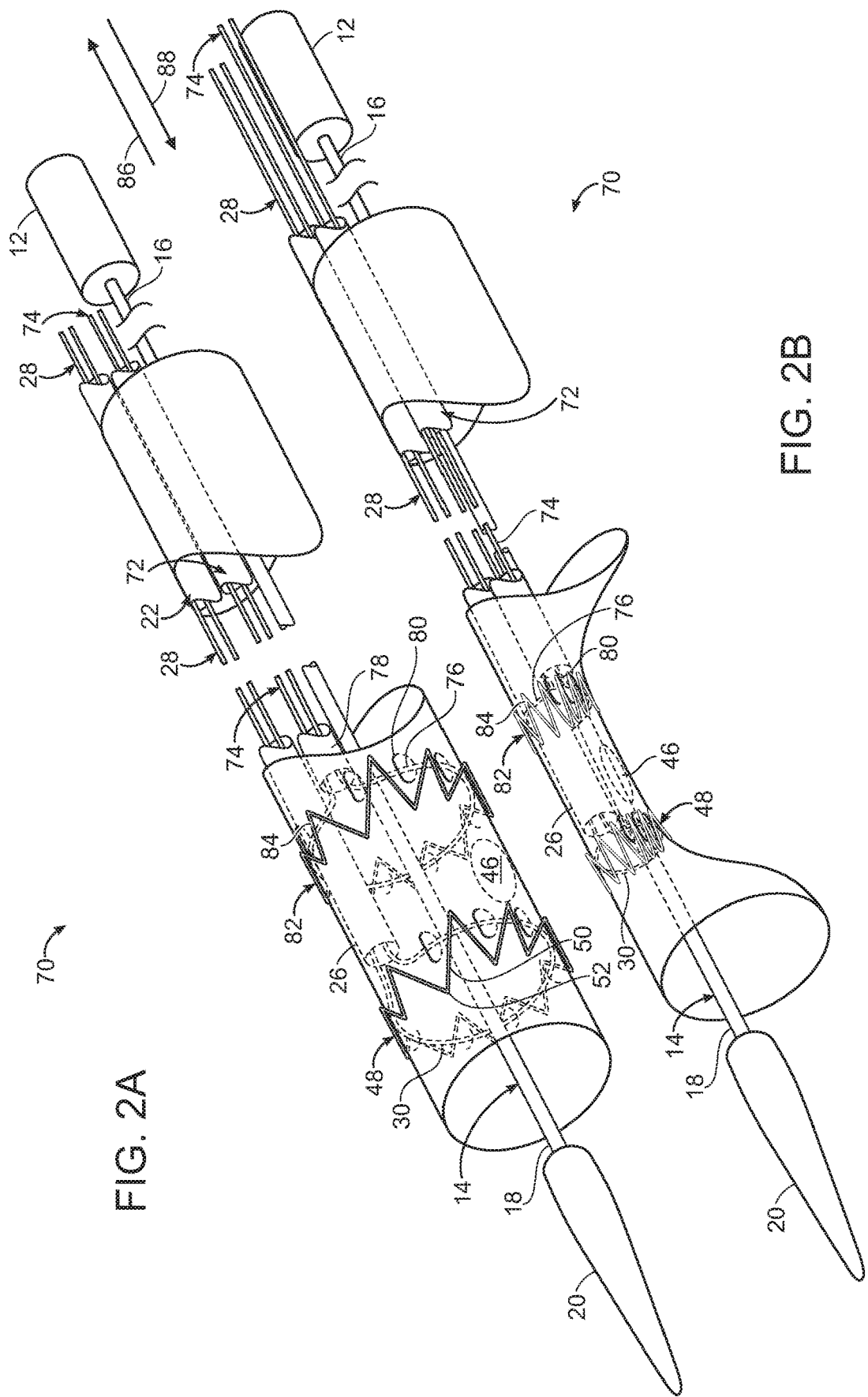

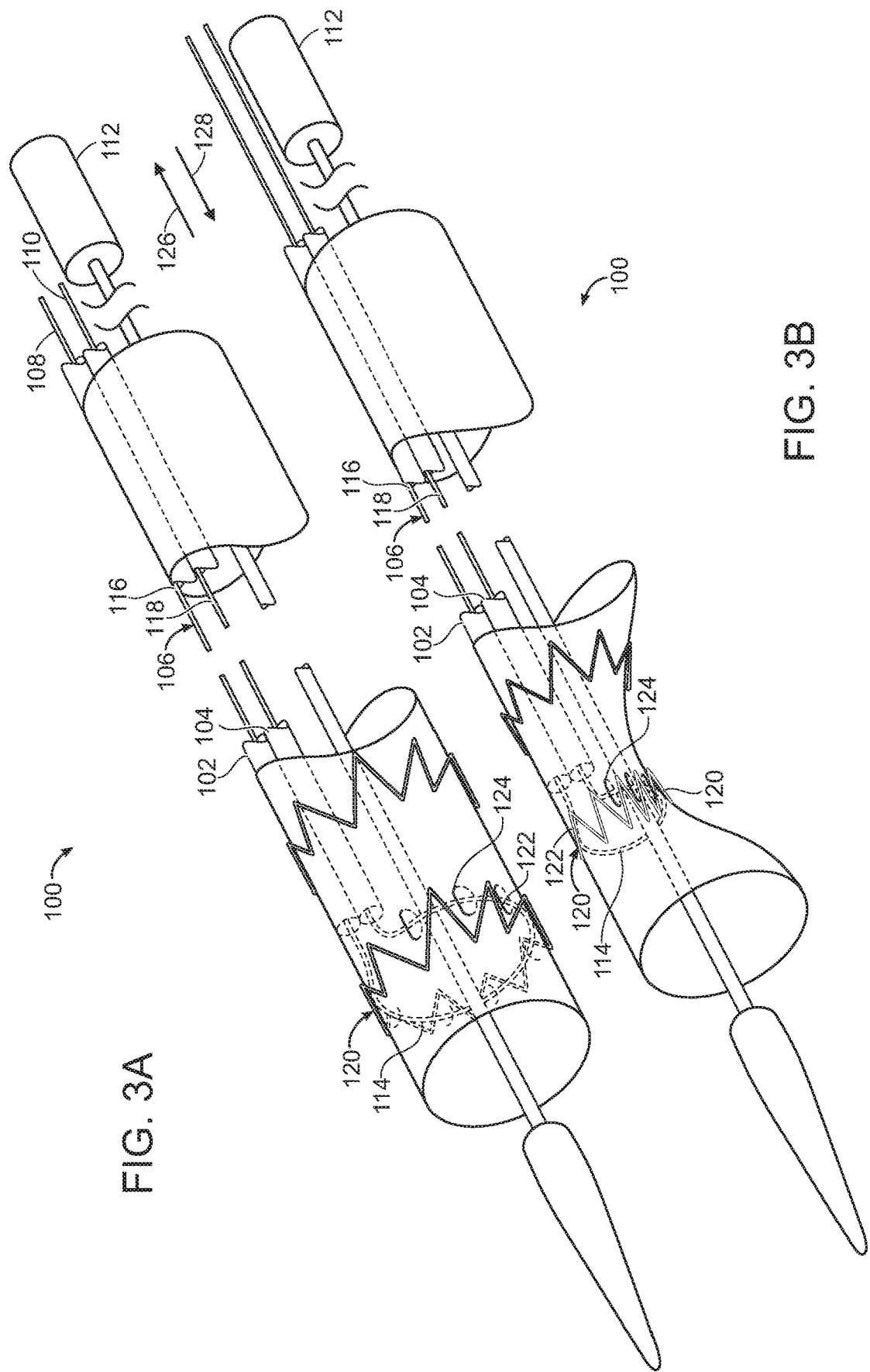

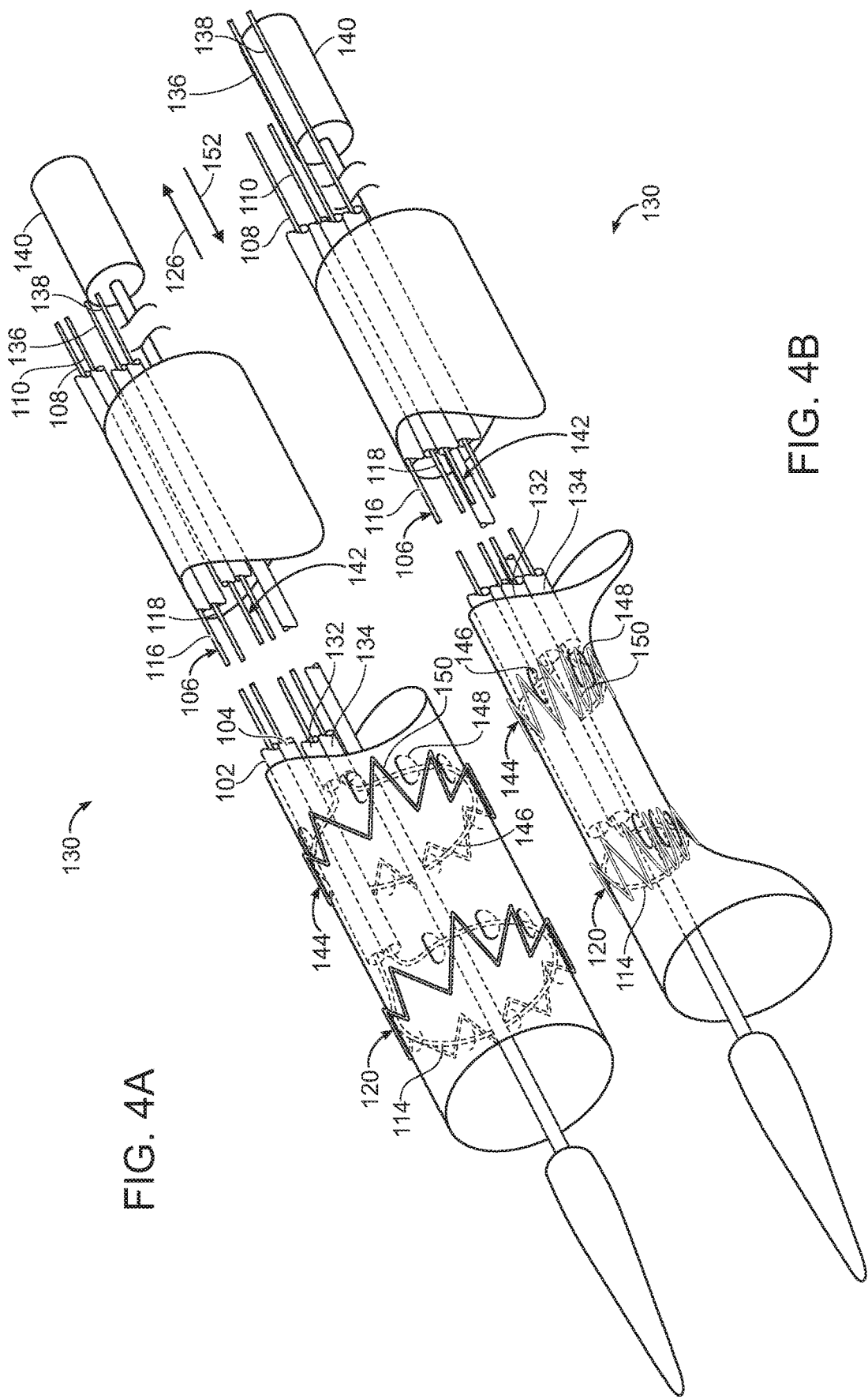

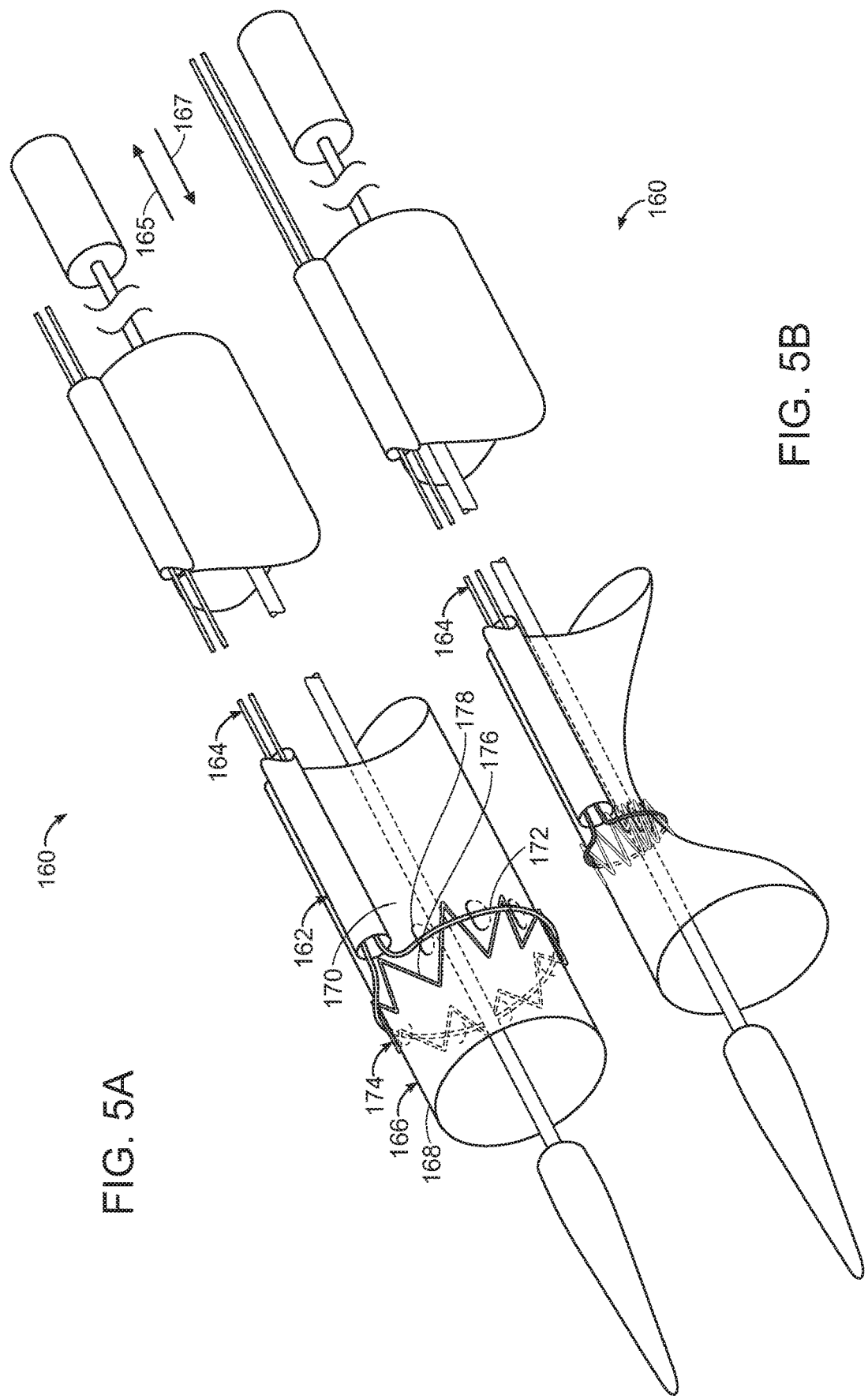

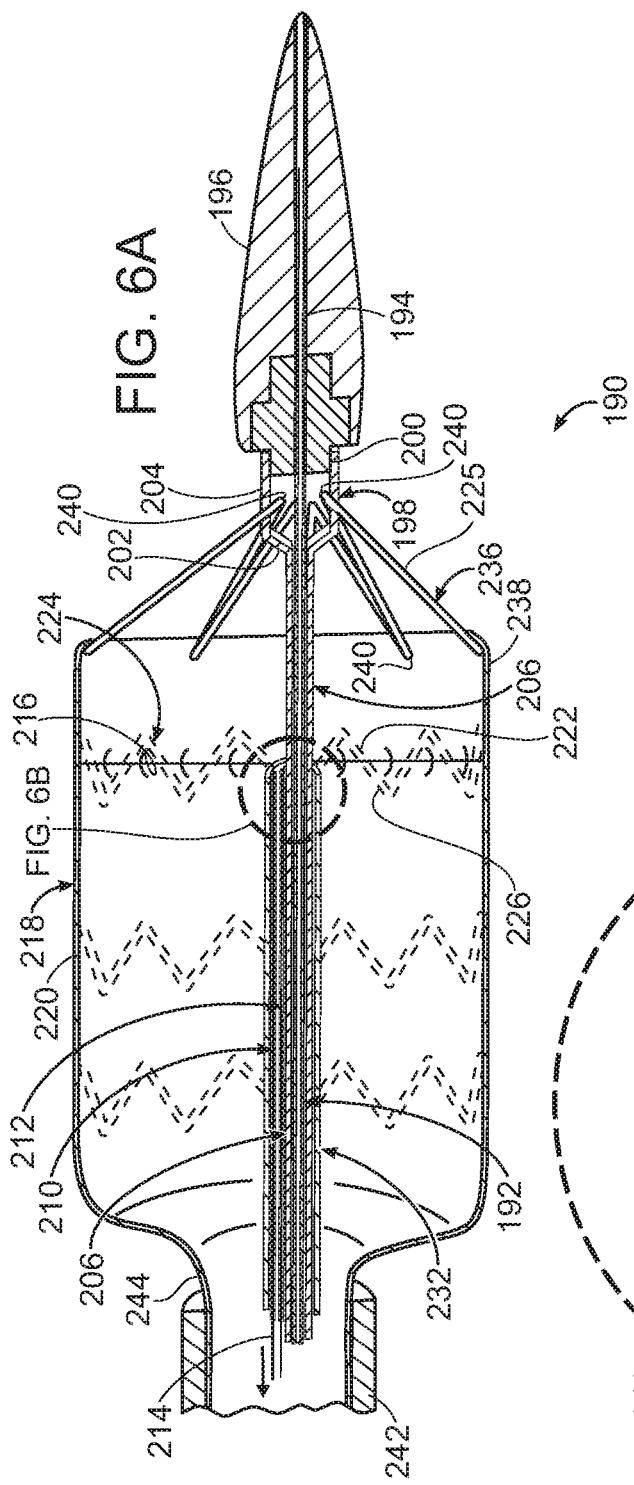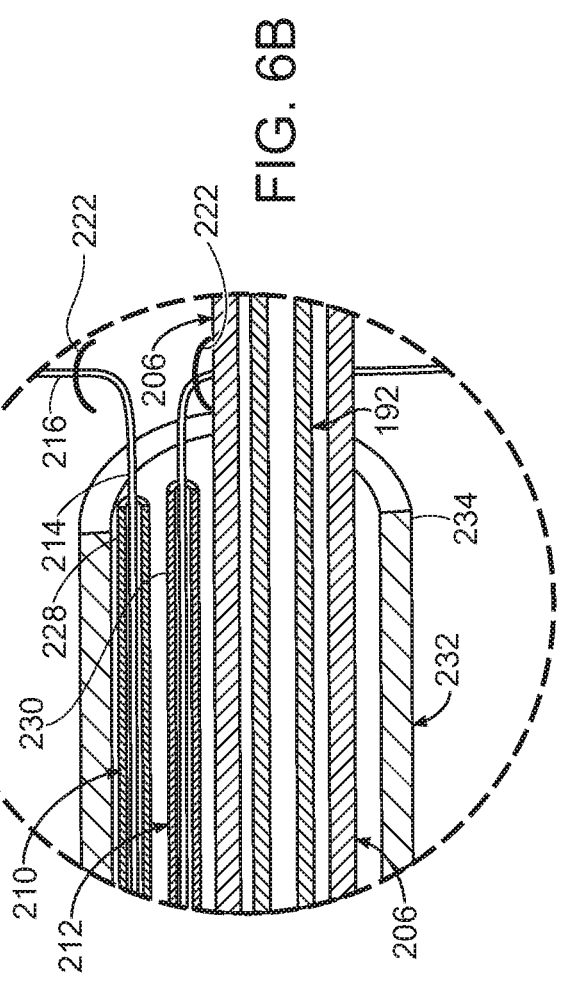

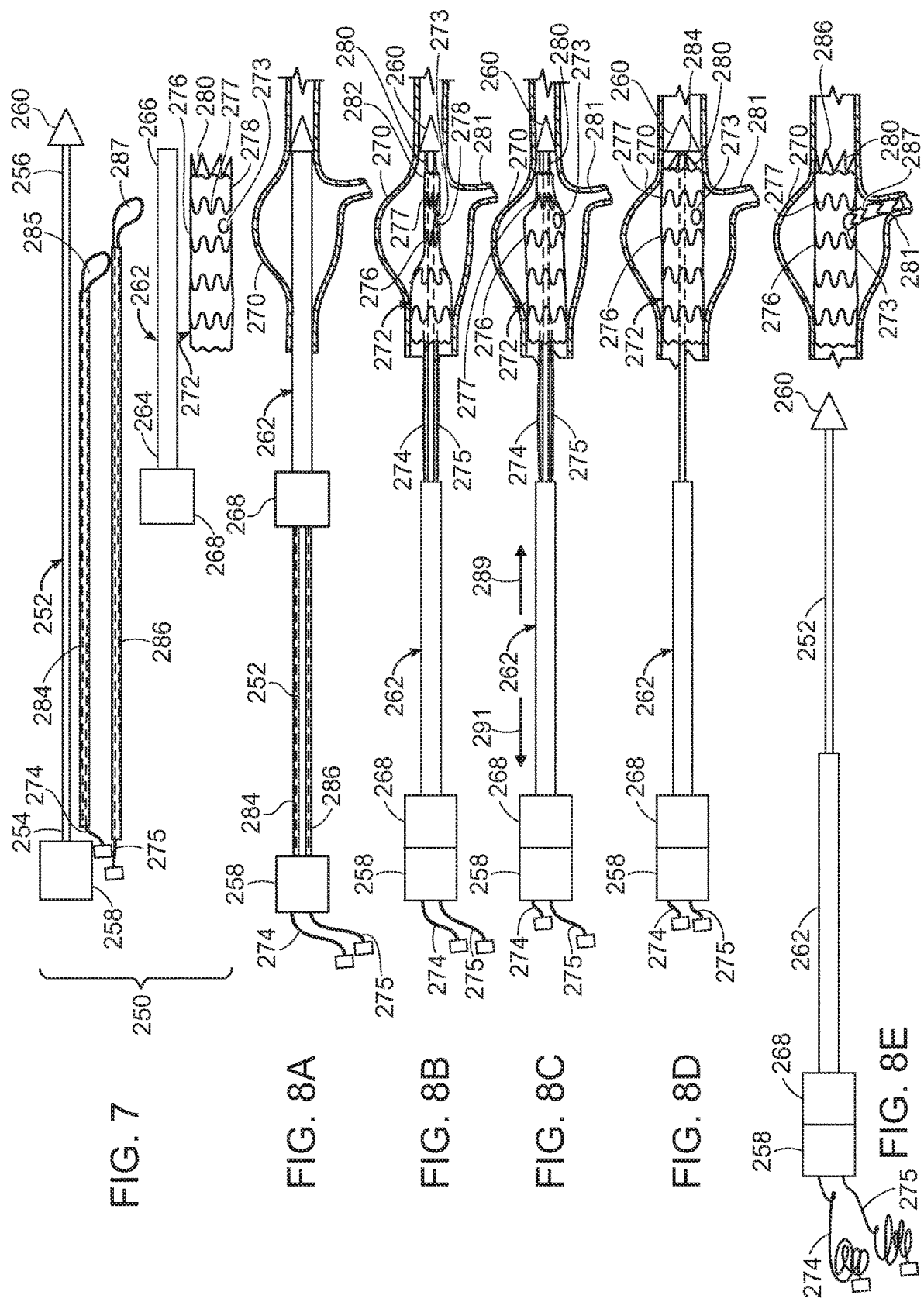

METHOD OF USE FOR DELIVERY SYSTEM FOR RADIALLY CONSTRICTING A STENT GRAFT

RELATED APPLICATIONS

This application is a continuation of U.S. Application Ser. No. 17/690,775, filed Mar. 9, 2022, which is a continuation of continuation of U.S. application Ser. No. 16/379,423, filed Apr. 9, 2019, which is a continuation of International Application No. PCT/US2018/019355, which designated the United States and was filed on Feb. 23, 2018, published in English, which claims the benefit of U.S. Provisional Application No. 62/463,018, filed on Feb. 24, 2017. The entire teachings of the above applications are incorporated herein by reference.

BACKGROUND

Aortic pathologies, including aortic aneurysms, can be treated by open surgical reconstruction, or alternatively, endovascular repair, which is a minimally invasive alternative to open surgical repair. Optimizing a successful outcome of endovascular repair, however, requires assessment of the patient's anatomy and, in the case of an aortic aneurysm, an appropriate stent graft that spans the proximal and distal ends of the aneurysm to insure complete exclusion of the aneurysm sac, anchoring of the stent graft in the aorta, and minimal endoleaks. Also, endoleaks and post-surgical enlargement of the aneurysm site can require additional repair to seal any expansion of the aneurysm sac, and, generally, must be done without significantly compromising blood flow through the surgical site to surrounding viscera and associated structures.

Therefore, a need exists for new and improved endovascular repair devices and methods to treat aortic pathologies, in particular aortic aneurysms.

SUMMARY

The present invention relates to stent graft delivery systems for use in treating and repairing aortic vascular damage, such as vascular damage associated with aortic aneurysms, including aortic aneurysms in regions of the aorta having arterial branches that supply blood to vital organs and tissues, such as thoracic aortic aneurysms, abdominal aortic aneurysms, thoracoabdominal aortic aneurysms, juxtarenal aortic aneurysms and short-neck abdominal aortic aneurysms.

In one embodiment, the stent graft delivery system includes a handle, a guidewire catheter, at least one tube and at least one wire. The guidewire catheter extends distally from the handle and includes a distal end. The tube includes a proximal end and a distal end. The at least one tube extends distally from the handle in parallel with guidewire catheter. At least one wire extends through the tube and is configured as a loop at the distal end of the tube. The wire includes at least one proximal end at the handle.

In another embodiment, the invention is a method of implanting a stent graft at an aneurysm of a subject, including the step of directing a stent graft to an aneurysm of the subject, and at least one stent of the stent graft being held in a radially constricted position by at least one wire configured as a loop that extends through at least one tube and is at least partially secured to the stent graft in a delivery system. The proximal end of the wire is variably moved in a proximal or distal direction to variably decrease or increase radial constriction of the at least one stent of the stent graft to assist axial and longitudinal alignment of the stent graft at the aneurysm site to thereby implant the stent graft at the aneurysm site.

This invention has many advantages. For example, the physician can selectively constrict the radial dimension of a partially deployed stent graft, thereby enabling the physician to rotate or otherwise reposition the stent graft after it has been partially deployed, such as by decreasing or increasing tension on at least one wire configured as a loop that is secured to a stent graft, thereby providing greater control over orientation of the stent graft before deployment. As a consequence, a stent graft can be deployed at an aneurysm with more accuracy, less risk of injury to the vasculature of the subject, and without significant risk of distorting the intended shape of the stent graft when implanted at the aneurysm.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments. The same number in different figures represents the same item.

FIG. 1A is a partial view in perspective of one embodiment of a stent graft delivery system of the invention, wherein a stent graft in a radially expanded position is secured by a wire extending through at least one tube and configured as a loop passing through sutures of the stent graft disposed between struts of a stent of the stent graft.

FIG. 1B is a perspective view of the embodiment shown in FIG. 1A, wherein a proximal end of the wire has been retracted to thereby radially constrict the stent graft, the struts of which are spanned by the wire, thereby selectively constricting the stent graft.

FIG. 2A is an embodiment of the stent graft delivery system of the invention having two wires, each spanning a different stent arranged longitudinally along a stent graft.

FIG. 2B is a perspective view of the embodiment shown in FIG. 2A, wherein both wires have been retracted to thereby radially constrict each associated stent of the stent graft.

FIG. 3A is a perspective view of an alternative embodiment of the stent graft delivery system of the invention, wherein the wire is partially contained in distinct tubes running parallel to a guidewire catheter of the stent graft delivery system.

FIG. 3B is a perspective view of the embodiment shown in FIG. 3A, wherein the wire has been retracted to thereby radially constrict the stent, the struts of which are spanned by the wire, thereby selectively radially constricting the stent graft.

FIG. 4A is a perspective view of another embodiment of a stent graft delivery system, wherein each of two wires are housed within separate tubes on either end of a loop spanning struts of stents of a stent graft.

FIG. 4B is a perspective view of the stent graft delivery system shown in FIG. 4A, wherein both wires have been retracted, thereby radially constricting the respective stent components, struts of which are spanned by each associated wire loop.

FIG. 5A is a perspective view, like the embodiment shown in FIG. 1A, but with the tube and the wire extending along an outside surface of the stent graft.

FIG. 5B is a perspective view, like the embodiment shown in FIG. 1B wherein a stent of the stent graft is radially constricted, but with the tube and the wire extending along an outside surface of the stent graft.

FIG. 6A is a cross-sectional view of a distal portion of another embodiment of the stent graft delivery system of the invention, that includes a proximal capture assembly, and following partial proximal retraction of an introducer sheath that fully contains a stent graft prior to proximal retraction.

FIG. 6B is a detail of the stent graft delivery system shown in FIG. 6A showing the arrangement of a guidewire catheter, an apex release catheter, tubes containing ends of the wire, a stent the struts of which are spanned by the wire as a loop, and an outer tube extending around a guidewire catheter, apex release catheter and tubes containing the wire.

FIG. 7 is an exploded view of one embodiment of components of a stent graft delivery system of the invention.

FIG. 8A is a side view of the stent graft delivery system shown in FIG. 7 when assembled.

FIG. 8B is a side view of the embodiment shown in FIG. 8A, following retraction of the proximal handle and introducer sheath to thereby expose a stent graft contained therein, and wherein the stent graft is radially constricted at each of two stents by separate wires that are radially controllable.

FIG. 8C is a side view of the embodiment shown in FIG. 8B, following distal movement of one of the wires, thereby radially expanding one of the stents of the stent graft.

FIG. 8D is a side view of the embodiment shown in FIG. 8C, following distal movement of both wires at the stents of the stent graft, thereby radially expanding both stents, but prior to release of proximal apices of a bare stent at a proximal end of the stent graft.

FIG. 8E is a side view of the embodiment shown in FIG. 8D, following release of the proximal apices of the bare stent at the proximal stent graft, and withdrawal of the stent graft delivery system of the invention.

DETAILED DESCRIPTION

Figure 6C:
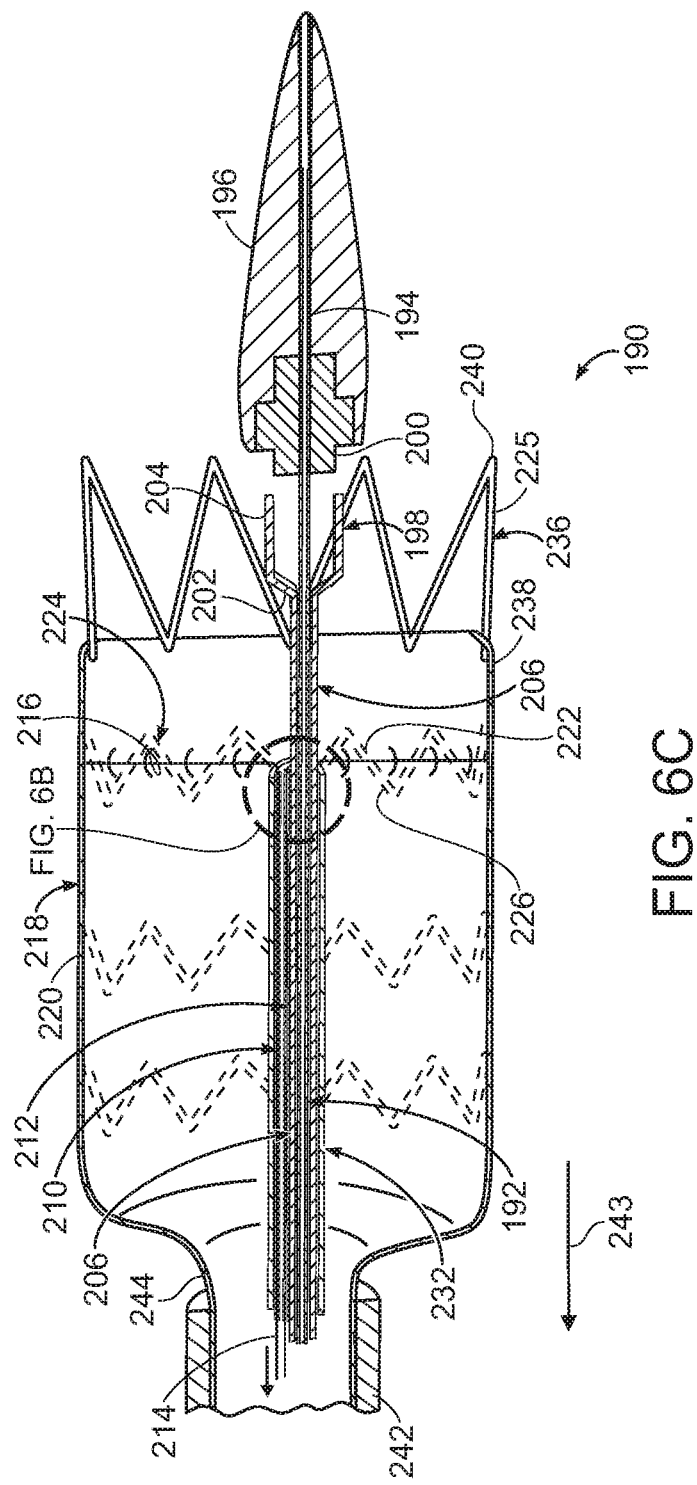
FIG. 6C is a cross-sectional view of a distal portion of the stent graft delivery system show in FIG. 6A following release of the proximal apices of the bare stent by retraction of the proximal capture portion from the distal capture portion of the apex capture assembly.

A description of example embodiments follows.

The invention generally is directed to a stent graft delivery system that includes at least one tube and at least one wire configured as a loop that extends through the tube and methods of use of the delivery system in treating and repairing aortic vascular damage, such as vascular damage associated with an aortic aneurysms, including in regions of the aorta having arterial branches that supply blood to vital organs and tissues, such as thoracic aortic aneurysms, abdominal aortic aneurysms, thoracoabdominal aortic aneurysms, juxtarenal aortic aneurysms and short-neck abdominal aortic aneurysms.

When reference is made herein to a prosthesis, also referred to herein as "stent graft," "stent graft prosthesis," or "vascular prosthesis," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

FIG. 1A is a perspective view of one embodiment of a stent graft delivery system of the invention, and of a stent graft to be delivered by the stent graft delivery system of the invention. As shown therein, the stent graft delivery system 10 includes handle 12, and guidewire catheter 14 extending distally from handle 12. Guidewire catheter 14 has proximal end 16 at handle 12 and distal end 18. Nose cone 20 is fixed to distal end 18 of guidewire catheter 14. Tube 22 extends distally from handle 12 and is substantially parallel to guidewire catheter 14. Tube 22 includes proximal end 24 at handle 12 and distal end 26. Wire 28 extends through tube 22 and is configured as loop 30 at distal end 26 of tube 22.

Stent graft 32 extends around guidewire catheter 14. Stent graft 32 includes proximal open end 34 and distal open end 36. Luminal graft component 38 of stent graft 32 has outside surface 40 and inside surface 42. Inside surface 42 defines graft lumen 44. In an embodiment, as appropriate, luminal graft component 38 defines fenestration 46, such as is shown in outline. Luminal graft component 38 is fabricated of a suitable material, such as is known to those skilled in the art, including, for example, expanded polytetrafluoroethylene (ePTFE), and polyethylene terephthalate (PET), such as woven polyester.

Stents 31,48 are distributed along outside surface 40 of luminal graft component 38. As shown, stents 31,48 include struts 50 that are joined at their respective ends to define proximal apices 52 and distal apices 54. Sutures 56 are distributed between struts 50 of stent 48 at distal end 26 of tube 22, also referred to herein as "nested." Loop 30 of wire 28 extends through sutures 56, thereby spanning struts 50 of stent 48. As shown in FIG. 1A, wire 28 is in a relaxed position, whereby loop 30 does not radially constrict stent 48 of stent graft 32.

As shown in FIG. 1B, proximal retraction of wire 28 through tube 22 in the direction indicated by arrow 58 causes radial constriction of loop 30 and, consequently, radial constriction of stent 48 spanned by loop 30 extending through sutures 56. In one embodiment, stent 48 is radially self-expanding, whereby release and proximal retraction of wire 28 enables selective constriction and radial expansion of stent 48, thereby enabling alternation in either proximal direction 58 or distal direction 60 between the configurations shown in FIG. 1A and FIG. 1B. In one embodiment, stents 31,48 are fabricated of a material that causes stents to radially self-expand upon release from radial constraint. Examples of suitable materials of radial self-expanding stents include a shape memory alloy, such as Nitinol. Examples of stents 31,48 not formed of a shape memory alloy include those formed of stainless steel. In embodiments of the invention that do not employ a shape memory alloy, or are otherwise not self-expanding, a balloon catheter, for example, can be employed to radially expand stents that have been released from radial constriction, as is known in the art. Alternatively, wire 28 can have sufficient rigidity to force radial expansion of stent 48 by directing the portion of wire 28 that extends through tube 22 in a distal direction indicated by arrow 60.

In another embodiment, stent graft delivery system 70, shown in FIG. 2A, resembles that shown in FIG. 1A, but further includes additional tube 72 and wire 74 arranged in parallel with guidewire catheter 14 and tube 22. Tube 72 contains wire 74 that is configured as loop 76 at distal end 78 of tube 72. Loop 76 is threaded through sutures 80, thereby spanning stent 82 at component struts 84. As shown in FIG. 2A, both wires 28,74 and associated stents 48,82 are shown in a relaxed (if radially self-expanding), or otherwise expanded position.

Components of the stent graft delivery system, such as the stents, wires, loops, tubes and sutures, can also include a radiopaque component, as is known in the art, such as at least one radiopacifier selected from the group consisting of barium sulfate, bismuth, tungsten, platinum-iridium and tantalum-tungsten.

FIG. 2B is a representation of the stent graft delivery system of FIG. 1A, wherein wires 28,74 have been retracted in a proximal direction, indicated by arrow 86, to thereby radially constrict both of stents 48,82. In the event that stents 48,82 are radially self-expanding, release of either or both of wires 28,74, will cause them to move in a distal direction indicated by arrow 88. It is to be understood that wires 28,74 can be controlled independently of each other, whereby either of stents 48,82 can be radially constricted by associated wire 28,74, respectively, while the other stent is in a relaxed, or expanded position. Further, each of wires 28,74 can be independently controlled so that either of wires 28,74 can each independently be maintained in a position that causes the associated stent to be in a fully radially expanded position, a fully radially constricted position, or any position between a fully radially expanded position and a fully radially constricted position.

FIG. 3A is a perspective view of an alternate embodiment of a stent graft delivery system of the invention. As shown therein, stent graft delivery system 100 includes two tubes 102,104 arranged in parallel. Wire 106 has portions that extend through tubes 102, 104, and includes ends 108, 110 at handle 112. Wire 106 includes loop 114 that links portions 116,118 of wire 106 extending through each of tubes 102, 104, respectively. Retraction of either or both portions 116,118 of wire 106 extending through either or both of tubes 102,104, respectively, causes radial constriction of stent 120 by constriction of struts 122 which are spanned by wire 106 extending through sutures 124 located between struts 122.

FIG. 3B is a representation of the stent graft delivery system of FIG. 3A, following proximal retraction in the direction indicated by arrow 126, of one or the other, or of both portions of wire 106 extending through tubes 102, 104, thereby causing radial constriction of stent 120. As with the embodiments shown above, stent 120 can be fabricated of a suitable material, whereby stent exhibits radial self-expansion, thereby enabling selective release and retraction of wire through either or both of tubes 102,104, and consequent alternation in either proximal direction 126 or distal direction 128 between radial expansion and radial constriction of stent 120 shown in FIGS. 3A and 3B, or positions therebetween.

Stent graft delivery system 130 of the invention shown in FIG. 4A resembles that of FIG. 3A, but includes additional tubes 132,134. Additional wire 142 extends through tubes 132, 134 and includes ends 136, 138 at handle 140. Wire 142 spans stent 144 at loop 146, which is distal to stent 120. Radial constriction of stent 144 is controllable by proximal and distal movement of wire 142. Connecting loop 146 is threaded through the sutures 148 between struts 150, thereby causing wire 142 to span struts 150 of stent 144.

As with the embodiment shown in FIGS. 2A and 2B, wires 106, 142 can be independently controlled to radially constrict or expand stents 120,144. As shown in FIG. 4B, both stents 120,144 are shown in a radially constricted position relative to that of FIG. 4A. Stents 120, 144 can each independently be held or maintained in a radially expanded or radially constricted configuration, or any partially radially constricted position therebetween. More specifically, the positions shown of stents in FIGS. 4A and 4B each can be changed by selective control of wires 106,142 in proximal and distal directions shown by proximal arrow 126 and distal arrow 152, respectively.

It is to be understood that additional wires and connecting loops can be included in additional embodiments of the invention, all of which can be adjusted independently to variably radially constrict or radially expand corresponding stents extending along the luminal graft component of a stent graft. Also, as can be seen in FIGS. 5A and 5B, in another delivery system 160 of the invention, tube 162 through which wire 164 extends can be arranged along stent graft 166 at luminal graft component 168 along outside surface 170. When arranged along outside surface 170 of luminal graft component, connecting loop 172 extends about outside surface 170 of luminal graft component 168, as well as stent 174 at struts 176. Sutures 178 are located between the struts 176, and wire 164 is threaded through sutures 178 at loop 172. Wire 164 can be retracted proximally in direction 165 or, in the case of self-expanding stent 174, moved in distal direction 167, to radially constrict or radially expand stent 174, respectively.

FIG. 6A is a cross-section of a distal portion of another embodiment of the stent graft delivery system of the invention, capable of radially constricting a stent graft prior to release from the stent graft delivery system. As shown in FIG. 6A, stent graft delivery system 190 has guidewire catheter 192 including distal end 194 and nose cone 196 fixed at distal end 194. Apex capture assembly 198 includes distal apex capture portion 200 fixed to distal end 194 of guidewire catheter 192. Proximal apex capture portion 202 includes tines 204, and apex release catheter 206 includes distal end 208 to which proximal apex capture portion 202 is fixed. Tubes 210,212 extend along apex release catheter 206 and in parallel with both apex release catheter 206 and guidewire catheter 192. Wire 214 at connecting loop 216 secures stent graft 218 at luminal graft component 220 by sutures 222. Sutures 222 are spaced at stent 224 between struts 226, thereby causing loop 216, which is threaded through sutures 222, to span struts 226 of stent 224. As can be seen more clearly in FIG. 6B, which is a detail of FIG. 6A, wire 214 extends through tubes 210,212 and portions of wire 214 extending through each tube 210,212 are linked by connecting loop 216 at distal ends 228,230 of tubes 210,212, respectively. Outer tube 232 extends about tubes 210,212, apex release catheter 206, and guidewire catheter 192, thereby fixing the spatial relationship between tubes 210, 212, apex release catheter 206, and guidewire catheter 192, relative to each other. Distal end 234 of outer tube 232 is located at about the same point along guidewire catheter 192 as that of distal ends 228,230 of tubes 210,212.

Returning to FIG. 6A, stent graft 218 extends about outer tube 232, containing tubes 210,212, and apex release catheter 206. Stent graft 218 includes luminal graft component 220, stents 224 which extend along luminal graft component 220, and bare stent 236 at proximal end 238 of luminal graft component 220. Bare stent 236 includes proximal apices 240 that are fixed at proximal apex capture portion 202 of apex capture assembly 198 by tines 204 extending between struts 225 defining proximal apices 240 of bare stent 236. Distal apices 240 of bare stent 236 are fixed to proximal end 238 of luminal graft component 220. Proximal apices 240 of bare stent 236 are released by retraction of apex release catheter 206 and, consequently, proximal apex capture portion 202, away from distal capture portion 200, thereby retracting tines 204 from between struts 225 of bare stent 236, whereby bare stent 236, formed of a shape memory alloy, such as nitinol, expands upon release of proximal apices 240 from constraint by tines 204. FIG. 6C is a cross-sectional view of the embodiment shown in FIG. 6A. Bare stent 236 is released from stent graft delivery system 190 by actuation of apex capture assembly 198.

Introducer sheath 242 at distal end 244 of luminal graft component 220 radially constricts distal end 244 of stent graft 218, and partially radially constricts stent graft 218 following partial distal retraction of introducer sheath 242 in the direction indicated by arrow 243 from stent graft 218, as described below with reference to FIGS. 7 and 8A through 8E.

FIG. 7 is an exploded view of components of another embodiment of a stent graft delivery system of the invention. As shown therein, stent graft delivery system 250 has guidewire catheter 252 includes proximal end 254 and distal end 256. Proximal handle 258 is fixed to proximal end 254 and nose cone 260 is fixed to distal end 256 of guidewire catheter 252. Introducer sheath 262 includes proximal end 264 and distal end 266. Distal handle 268 is fixed to proximal end 264 of introducer sheath 262. Wires 274,275 have sufficient length to extend from stent graft 218 to proximal handle 258, and are housed in respective tubes 284,286, respectively. Loops 285,287 extend distally from tubes 284,286.

FIG. 8A is a representation of the component parts shown in FIG. 7 in assembled form. When assembled, tubes 284, 286 are fixed at respective proximal handle 258, as well as one end of each of wires 274,275. The other end of each of wires 274,275 extends through handle 258 and is proximally retractable to thereby radially constrict stent graft 272 at stents 277 spanning sutures through which wire loops 285, 287 are threaded. Introducer sheath 262 extends around distal end 256 of guidewire catheter 252. Although not shown, a stent graft 272 is contained within introducer sheath 262. In one embodiment of a method of the invention, stent graft delivery device 250 is advanced within an artery of a patient until introducer sheath 262 and a vascular prosthesis, such as a stent graft 272, contained within introducer sheath 262, are located at aneurysm 270 of a patient. Distal handle 268 and, consequently, introducer sheath 262, are retracted toward proximal handle 258, thereby at least partially exposing the stent graft 272, as shown in the transition from FIG. 8A to FIG. 8B. It is to be understood that, in an alternative embodiment, stent graft delivery system 250 can be advanced within an artery of a patient until introducer sheath 262 and stent graft 272 contained therein are located distal to aneurysm 270 of the patient. In this embodiment, proximal handle 258 and guidewire catheter 252, to which stent graft 272 is directly or indirectly fixed, are advanced distally toward distal handle 268, whereby stent graft 272 is at least partially advanced from introducer sheath 262 to aneurysm 270, resulting in the representation shown in FIG. 8B.

In either embodiment, wires 274,275 of stent graft delivery system of the invention constrict stent graft 272 at stents 276,277, respectively. As shown in FIGS. 8B and 8C, wires 274,275 radially constrict stents 276,277 at distal end 278 of stent graft 272. In an embodiment, stent graft 272 includes fenestration 273. Stents 276,277 can be selectively controlled by proximal and distal movement of wires 274,275, as is shown in the transition from FIG. 8B to FIG. 8C, which shows stent 276, distal to stent 277, exhibiting radial expansion as a consequence of distal movement of wire 274 in the direction of arrow 289, such as by relaxation of tension of wire 274 having a loop extending about stent 276, causing radial expansion of stent 276. Only stent 277 remains radially constricted, as shown in FIG. 8C. In the instance where stents 276,277, respectively are radially self-expanding, such as where stents are fabricated of a suitable shape memory alloy, such as Nitinol, relaxation of tension on wires 274,275 will cause radial expansion of stents 276,277, respectively. Alternatively, where stents 276,277 are not radially self-expanding, then stents 276,277 can be radially expanded by employing wires 274,275 that are sufficiently rigid to force radial expansion of stents 276,277, or by employing a balloon catheter (not shown), such as is known in the art.

It is also to be understood that wires 274,275 radially constricting each of stents 276,277 could be released in reverse order, thereby causing stent 277 to exhibit radial expansion while stent 276 remains constricted by associated wire 274. Further, either or both of stents 276,277 can be radially constricted by moving each respective wire in a proximal direction indicated by arrow 291. Also, wires 274,275 can be controlled independently of each other whereby tension on each wire is independently and variably controlled to adjust radial expansion of associated stents during proper rotational and longitudinal adjustment of stent graft at aneurysm site. In still another embodiment, the stent graft delivery system of the invention may include only one wire, as described above, thereby resulting in constriction of only one stent.

Upon release or distal movement of both wires 274,275 radially constricting each respective stents 276,277 of stent graft 272, stents 276,277 will both exhibit radial expansion to occupy aneurysm 270 of the subject. In the embodiment wherein stent graft 272 includes bare stent 280 at proximal end 282 of stent graft 272, bare stent 280 can remain fixed at apex capture assembly 284, as shown in FIG. 8D. In this embodiment, release of proximal apices 286 of bare stent 280 by actuation of apex capture assembly 284 causes bare stent 280 to land at a portion of the artery just cranial to aneurysm 270. As shown in FIG. 8E, wires 274,275 can be removed at any time following release of tension on wires 274,275 to allow radial expansion of stents 276,277 by, for example, pulling on one end of each wire 274,275 to thereby retract the wire from the remainder of stent graft delivery system 250, or by severing connection of wires 274,275 from proximal handle 258. Thereafter, the remainder of stent graft delivery system 250 can be retracted from within stent graft 272 and from the patient, thereby completing implantation of stent graft 272 and treatment of aneurysm 270, as also shown in FIG. 8E. In an embodiment, stent graft 272 is positioned so that fenestration 273 is properly aligned with arterial branch 281 for subsequent placement of branch prosthesis 287 through fenestration 273 to arterial branch 281. Thereafter, stent graft 272 is fully implanted within aneurysm 270, and the remainder of stent graft delivery system 250 is retracted from stent graft 272 and the patient, as shown in FIG. 8E, thereby completing treatment of aneurysm 270 of the patient by the method of the invention.

Figure 9A:
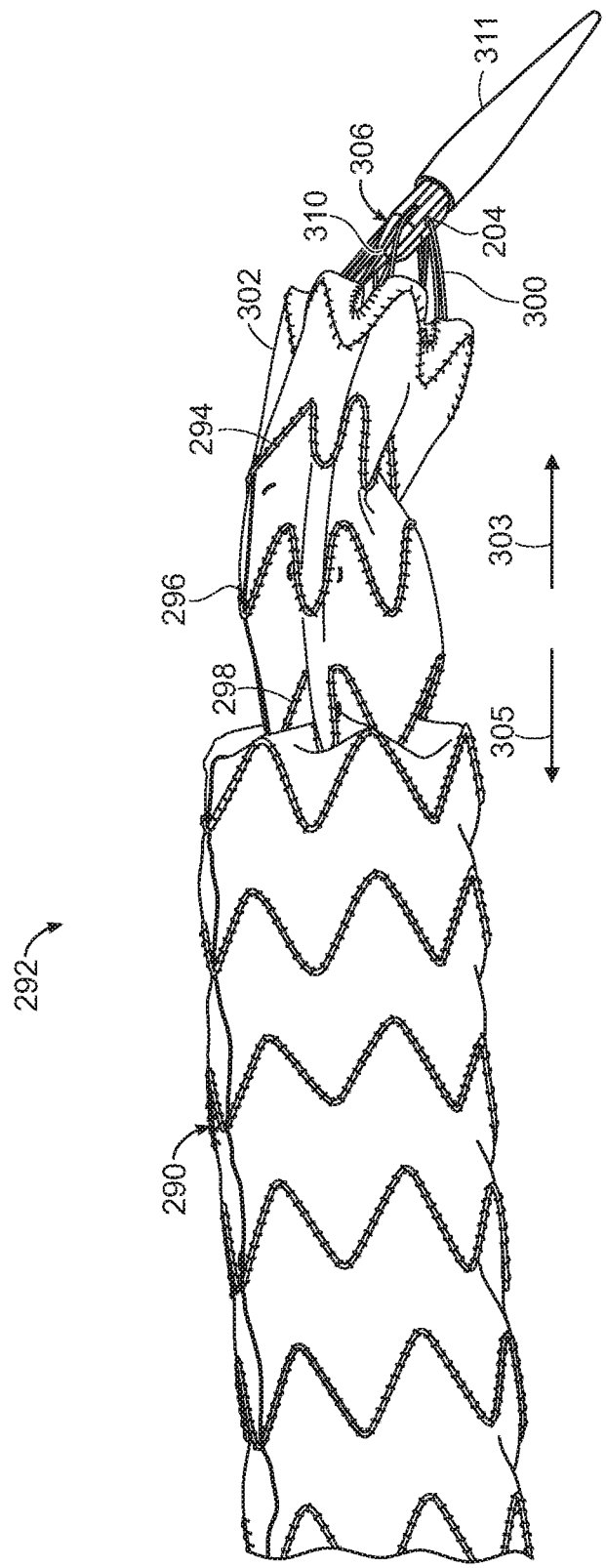
FIG. 9A is a partial side view of a stent graft prior to distal movement of wires spanning each of three stents at a proximal end of a stent graft.

FIG. 9A is a partial side view of a portion of stent graft prosthesis 290 of stent graft delivery system 292 of the invention showing radial constriction of three stents 294, 296,298 by respective wires (not shown) within stent graft prosthesis 290. Bare stent 300 at proximal end 302 of prosthesis 290 is fixed at proximal apices 204 of bare stent 300 by apex capture assembly 306. As can also be seen in FIG. 9A, guidewire catheter (not shown) is arched, thereby causing stent graft prosthesis 290 to be arched at distal end 310. Nose cone 311 is at distal end 310 of the guidewire catheter. It is to be understood that, in addition, stent graft prosthesis 290 may define at least one fenestration or scallop (not shown) between constricted stents 294,296,298, which, in this case, are radially self-expanding, whereby radial constriction of stents is determined by the tension on loops threaded through sutures between struts of stents 294,296, 298, as is described above. Configuring guidewire catheter 308 as an arch at its distal end 310 is beneficial in embodiments where fenestration (not shown) is located at an arcuate arterial blood vessel, such as the aortic arch. Independent change of tension on, or distal movement of, wires controlling loops (not shown) at each of respective stents 294,296,298 improves control by the surgeon during alignment and implantation of stent graft prosthesis 290. Distal movement of wires is indicated by arrow 303. Proximal movement of wires is indicated by arrow 305. Alignment of stent graft prosthesis 290 is also improved by the arch of guidewire catheter 308 which, during advancement of stent graft prosthesis 290 to the aneurysm site, facilitates rotational orientation of stent graft prosthesis 290 to thereby improve alignment of any fenestrations with arterial branches at the fenestration, such as arterial branches at an aortic arch.

Figure 9B:
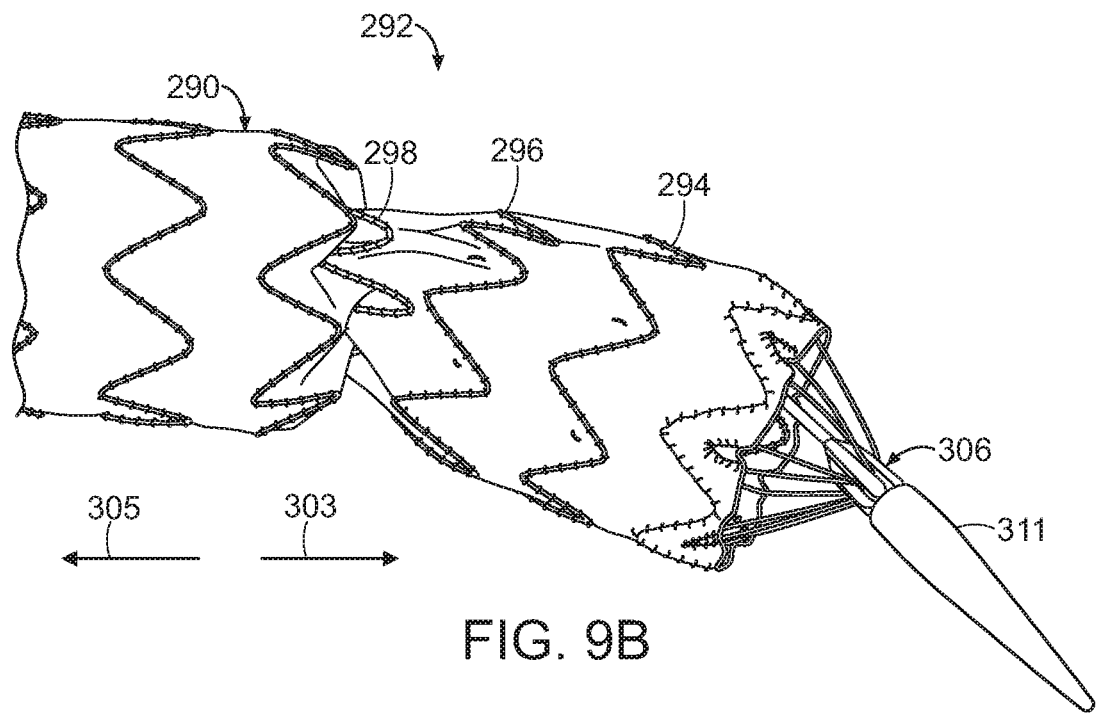
FIG. 9B is a partial side view of the stent graft shown in FIG. 9A, following selective distal movement of one wire to thereby radially expand the most distal stent component, previously shown radially constricted in FIG. 9A.
Figure 9C:
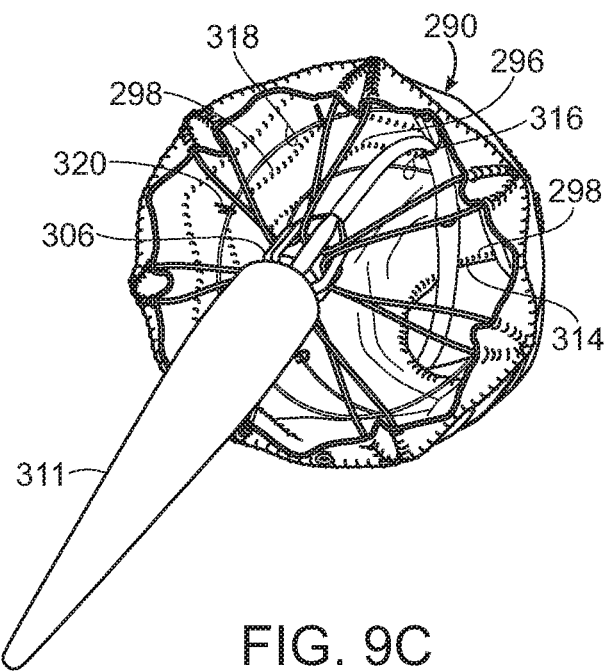
FIG. 9C is an end view of the stent graft and delivery system of FIG. 9A following the distal movement of a wire radially constricting the most proximal stent of the stent graft previously shown radially constricted in FIG. 9A.
Figure 9D:
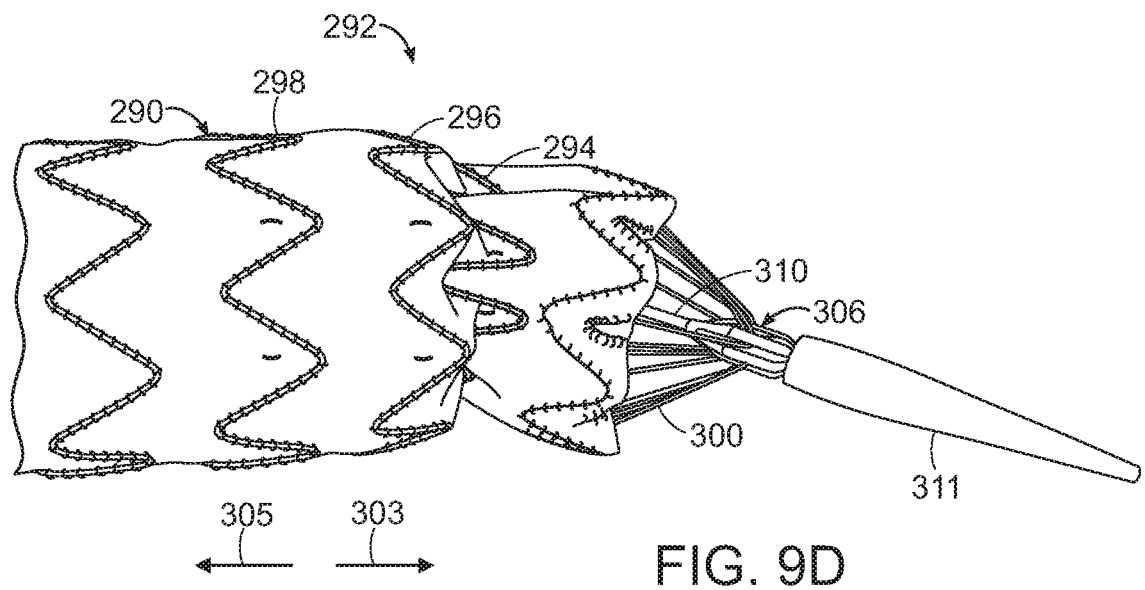
FIG. 9D is a side view of the stent graft shown in FIG. 9A, following distal movement of the wires previously shown radially constricting the two stents distal to the proximal radially constricted stent in FIG. 9A, but having been moved in a distal direction to radially expand those two stents, and before distal movement of the wire radially constricting the most proximal of the previously radially constricted stents.

FIG. 9B is a partial side view of stent graft prosthesis 290 and stent graft delivery system 292 shown in FIG. 9A, wherein two of three wires constricting respective stents 294,296,298 have been released, or moved distally, thereby enabling radial expansion of two stents 294,296 proximal to third stent 294 that remains in a constricted configuration by its respective constraining wire of the stent graft delivery system. FIG. 9C is an end view of the embodiment shown in FIG. 9B, wherein most distal wire 318 previously constricting stent 298, is relaxed, or moved distally, but remains threaded through sutures 320 at stent graft 290. FIG. 9D is a partial side view of stent graft prosthesis 290 of stent graft delivery system 292 shown in FIG. 9A, wherein tension on wires 314,316 previously constricting stents 294,296 to stent 298 has been relaxed, or moved distally, thereby enabling radial expansion of stents 294,296, while stent 298 remains in a radially constricted position.

Figure 9E:
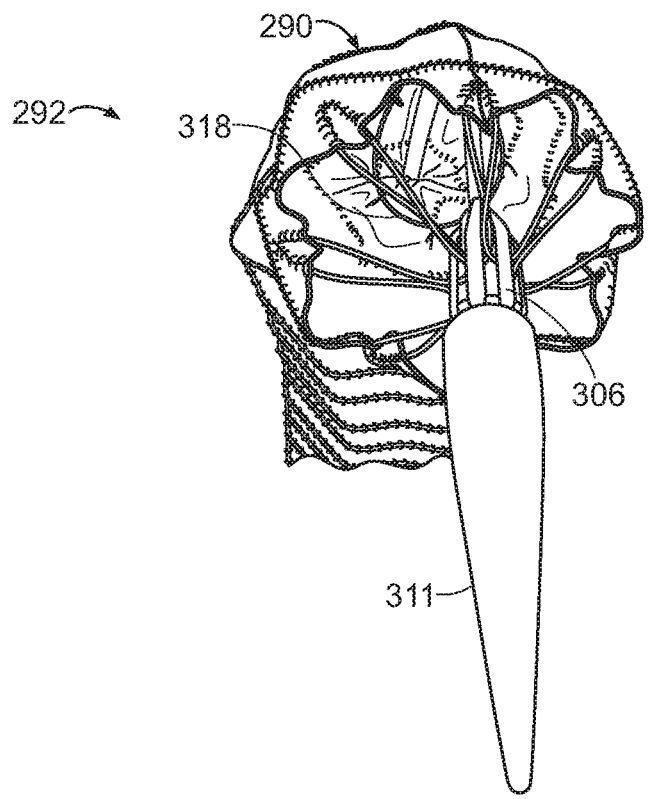
FIG. 9E is an end view of the stent graft shown in the configuration represented by FIG. 9D, which is prior to distal movement of the wire to thereby radially expand the most proximal of the stents previously shown radially constricted in FIG. 9A.
Figure 9F:
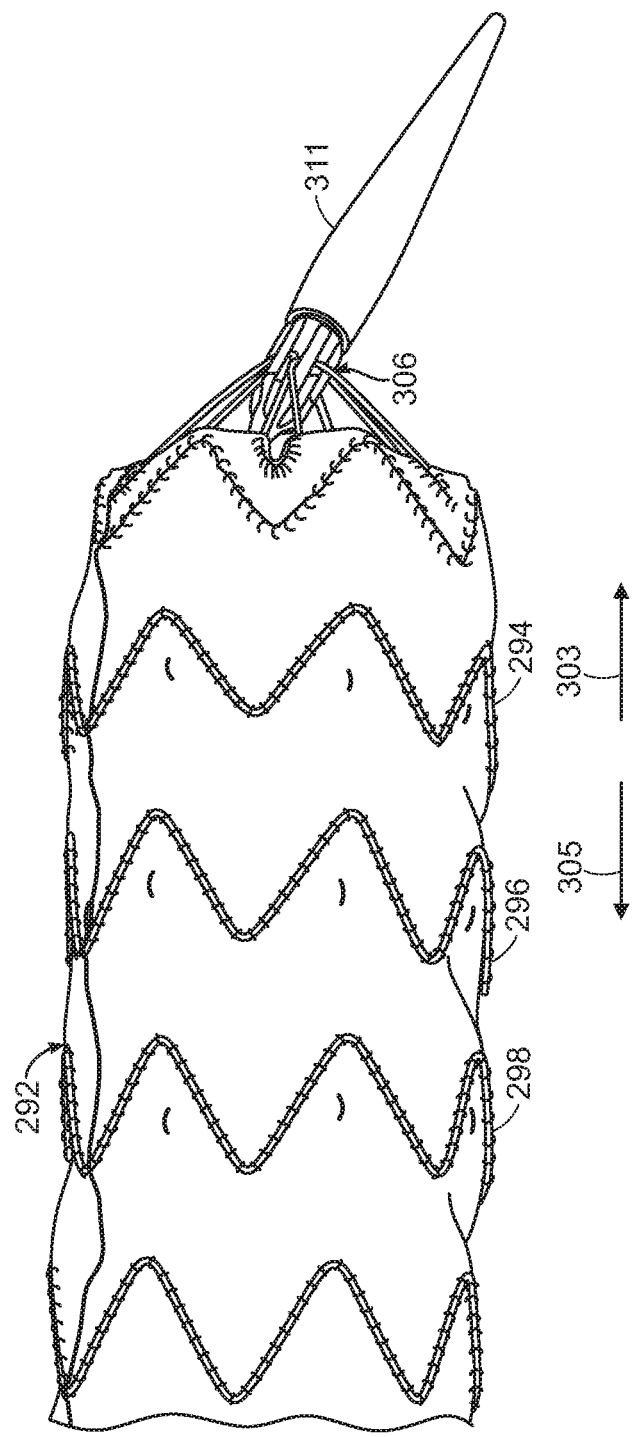
FIG. 9F is a partial side view of the stent graft and delivery system of FIGS. 9A-9E, following distal movement of all wires to thereby radially expand respective stents at the proximal end of the stent graft.
Figure 9G:
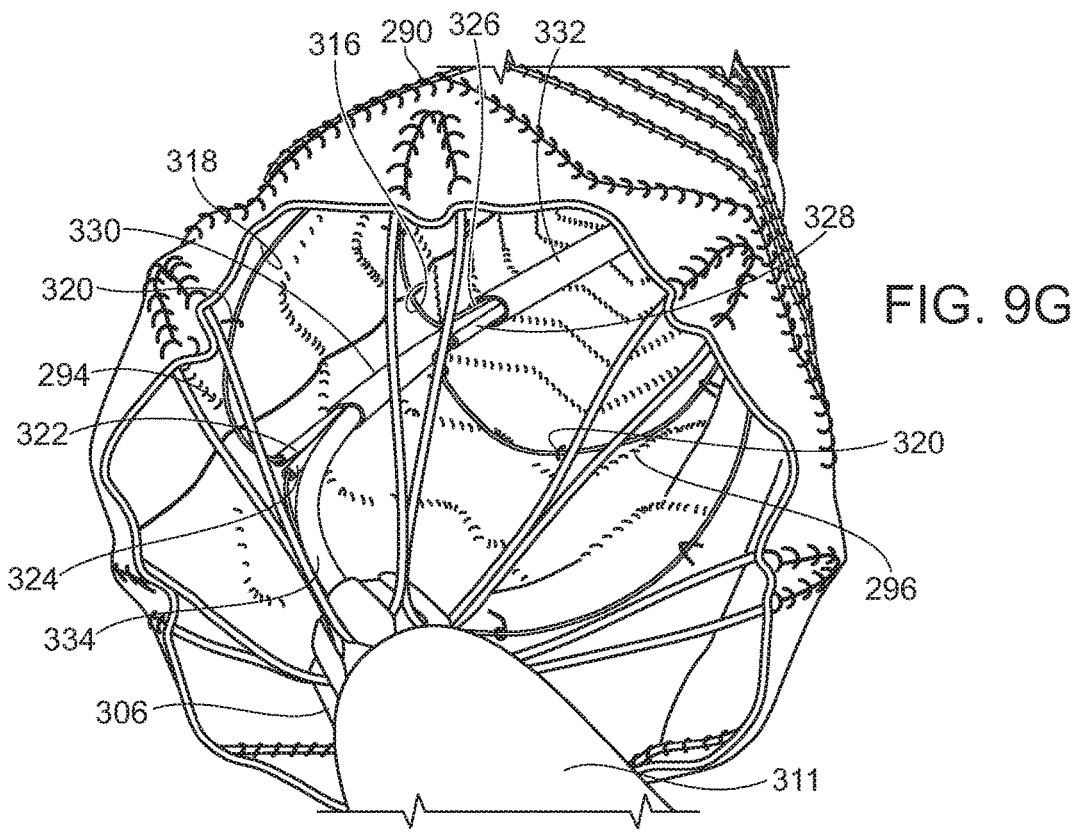
FIG. 9G is an end view of the stent graft and delivery system, as represented in FIG. 9F.
Figure 9H:
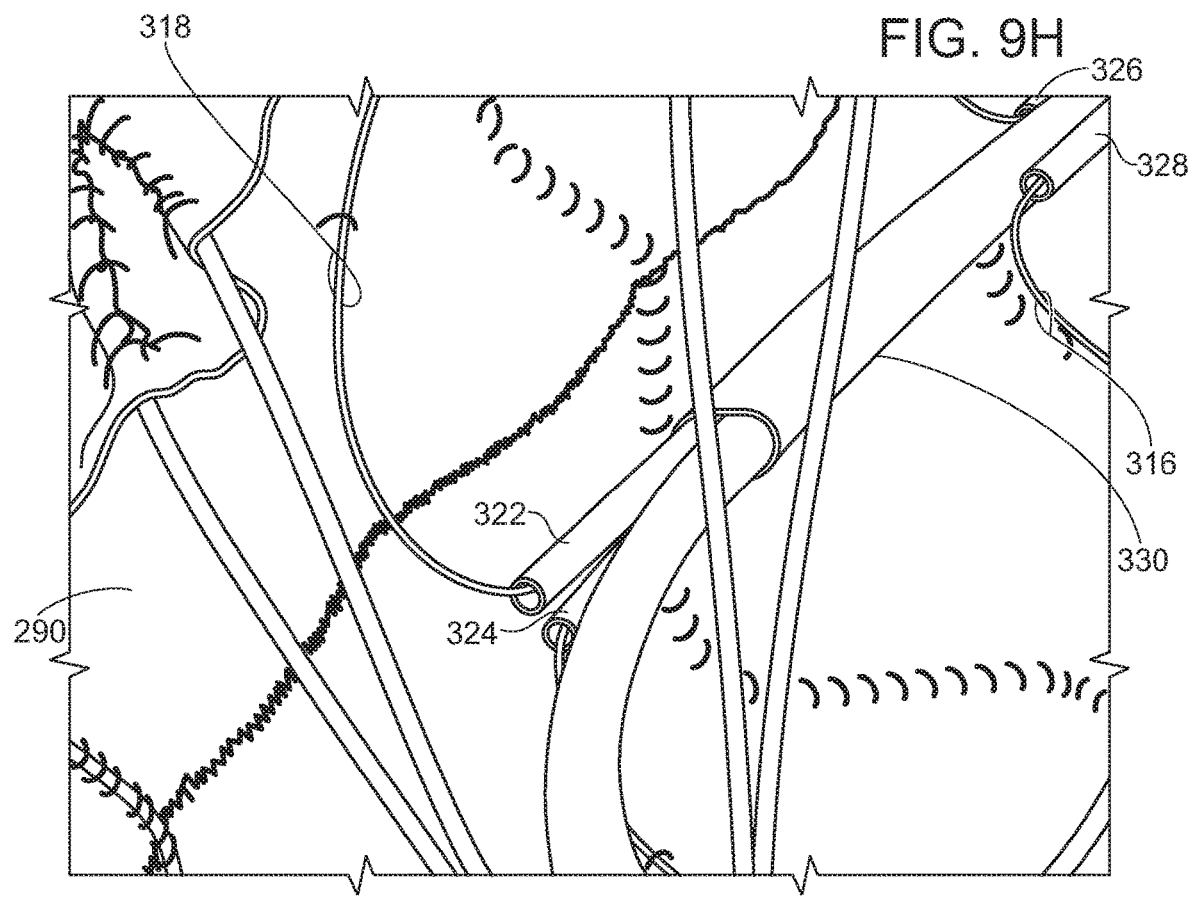
FIG. 9H is a detail of the representation shown in FIG. 9G, showing the arrangements of tubes containing wires that radially constrict the stents of the stent graft after distal movement of two of the wires previously radially constricting the stent.

FIG. 9E is an end view of stent graft 290 and delivery system 292 in the arrangement shown in FIG. 9D, wherein wire 318 constricting most proximal stent 298 is still in a constricted position. FIG. 9F is a side view of stent graft prosthesis 292 shown in FIGS. 9A through 9E, wherein the tension on all wires 314,316,318 previously constricting stents 294,296,298 has been relaxed. FIG. 9G is an end view of the configuration of stent graft prosthesis shown in FIG. 9F, wherein the two most distal wires 316,318 extending through sutures 320 at stents 294,296 have been relaxed, or moved distally, but remain threaded through sutures 320 at stent graft 290 between the struts of stents 294,296,298. Inner tube 330 extends about tubes 322,324, and apex release catheter 334. Outer tube 332 extends about inner tube 330 and tubes 326,328. FIG. 9H is a detail of wires 316,318 extending from tubes 322,324 and of tubes 326,328 extending from inner tube 330.

Vascular prostheses implanted by the stent graft systems and methods of the invention can be implanted, for example, by transfemoral access. Additional branch prostheses that are directed into the vascular prostheses of the invention can be implanted, for example, by supraaortic vessel access (e.g., through the brachial artery), or by transfemoral access, or access from some other branch or branch of major blood vessels, including peripheral blood vessels.

The teachings of all patents, published applications and references cited herein are incorporated by reference in their entirety. The relevant teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712, 9,827,123, 9,877,857, 9,907,686; U.S. patent application Ser. Nos. 14/575,673; 15/166,818; 15/167,055; 14/272,818; 14/861,479; 15/478,424; 15/478, 737; 15/587,664; 15/604,032; 15/672,404; 15/816,772; 15/839,272; 15/417,467; PCT/US2017/025844; PCT/US2017/025849; PCT/US2017/025912; PCT/US2017/034223 and PCT/US2017/046062, are also incorporated by reference in their entirety.

The relevant teachings of PCT/US2018/019344; PCT/US2018/019349; PCT/US2018/019353; PCT/US2018/09354; PCT/US2018/019352; PCT/US2018/019342; PCT/US2018/019350; PCT/US2018/019356; PCT/US2018/019351; and PCT/US2018/01950, are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A stent graft delivery system, comprising:
a) a handle;
b) a guidewire catheter extending distally from the handle and having a distal end, a proximal end and a longitudinal axis, wherein the proximal end of the guidewire catheter is fixed to the handle;
c) at least one tube having a proximal end and a distal end, wherein the proximal end of the at least one tube is fixed to the handle, and the at least one tube extending distally from the handle and arranged in parallel with the guidewire catheter;
d) at least one wire extending through the at least one tube, wherein each wire is configured as a loop at the distal end of the at least one tube, and having at least one proximal end at the handle; and
e) a stent graft having
i) a proximal open end and a distal open end,
ii) a longitudinal axis,
iii) a luminal graft component having an inside surface defining a graft lumen,
iv) a plurality of stents each extending about the luminal graft component and distributed about the longitudinal axis of the luminal graft component, wherein at least a portion of the stents include struts that are joined to define proximal apices and distal apices, and
v) a plurality of suture loops nested between the struts of the stents, wherein the at least one wire extends through the suture loops to thereby secure the stent graft, wherein the stent graft extends about the guidewire catheter, and wherein the loop of the at least one wire at least partially secures the stent graft, whereby retraction of the at least one wire extending through the suture loops causes radial constriction of the stent graft at the suture loops.

2. The stent graft delivery system of claim 1, wherein the at least one tube is a first pair of tubes arranged in parallel and the at least one wire extends through the two tubes, the loop linking a portion of the at least one wire extending within each respective tube of the first pair of tubes.

3. The stent graft delivery system of claim 2, wherein the stent graft includes a bare stent at the proximal end, and wherein the bare stent is secured at the distal end of the guidewire catheter.

4. The stent graft delivery system of claim 3, wherein the at least one wire includes two wires, wherein the loops of the respective wires of the two wires are arranged longitudinally along the longitudinal axis of the guidewire catheter relative to each other.

5. The stent graft delivery system of claim 1, wherein at least a portion of the at least one wires extend through the plurality of suture loops at the stent graft.

6. The stent graft delivery system of claim 5, wherein the plurality of suture loops are nested distally to the respective proximal apices of the respective stent.

7. The stent graft delivery system of claim 1, wherein the at least one wire includes at least two wires that extend through the suture loops at the stent graft.

8. The stent graft delivery system of claim 7, wherein each of the wires radially constrict a respective stent of the stent graft.

9. The stent graft delivery system of claim 8, wherein each of the wires extend through at least two sutures, each of which is nested distally to a proximal apex of a respective stent.

10. The stent graft delivery system of claim 8, wherein the wires are independently operable.

11. The stent graft delivery system of claim 8, further including a wire handle at one of the proximal ends of at least one respective wire, whereby each wire is operable by proximal retraction or advancement of the respective handle.

12. The stent graft delivery system of claim 11, wherein the plurality of wires are collectively fixed at the proximal ends to the wire handle, whereby distal or proximal movement of the wire handle in a longitudinal direction along the stent graft causes the wires to collectively increase or decrease radial constriction of the stent graft.

13. The stent graft delivery system of claim 11, wherein at least a portion of the wires are each independently fixed at their respective proximal ends to a distinct wire handle, whereby distal and proximal movement of each wire handle in a longitudinal direction along the stent graft causes the wires to act independently of the at least one other wire and the respective wire handle, to independently increase or decrease radial constriction of a corresponding portion of the stent graft at the respective suture loops through which each respective wire loop is threaded.

14. The stent graft delivery system of claim 1, wherein the at least one wire is formed of a shape-memory material.

15. The stent graft delivery system of claim 1, wherein the at least one wire is independently releasable from the remainder of the stent graft delivery system, whereby the at least one wire can be removed from the suture loops at the stent graft, thereby releasing the stent graft from the at least one wire.

16. The stent graft delivery system of claim 1, wherein the luminal graft component defines a fenestration.

17. The stent graft delivery system of claim 1, wherein the at least one tube is a first pair of tubes arranged in parallel and the at least one wire is a pair of wires that each extend through each of the tubes, the loop of each wire extending within each respective tube.

18. The stent graft delivery system of claim 1, wherein the stents are distributed along an outside surface of the stent graft.

19. The stent graft delivery system of claim 1, wherein the distal end of the at least one tube is within the stent graft.

20. The stent graft delivery system of claim 1, wherein the at least one tube extends along an outside surface of the luminal graft component.

* * * * *